US00PP17743P3

(12) United States Plant Patent
Pieters

(10) Patent No.: US PP17,743 P3
(45) Date of Patent: May 22, 2007

(54) ***CHRYSANTHEMUM* PLANT NAMED 'GEDI THREE CAMAN'**

(50) Latin Name: *Chrysanthemum morifolium*
Varietal Denomination: GEDI THREE CAMAN

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 204 days.

(21) Appl. No.: 11/095,800

(22) Filed: Mar. 30, 2005

(65) Prior Publication Data

US 2006/0225171 P1 Oct. 5, 2006

(51) Int. Cl.
*A01H 5/00* (2006.01)

(52) U.S. Cl. ..... Plt./287
(58) Field of Classification Search ..... Plt./287
See application file for complete search history.

(56) References Cited

PUBLICATIONS

Shukla et al., "Mutation studies on early and late varieties of garden *chrysanthemum*". 1993.J. Nuclear Agric. Biol., 23(3–4):138–142.*

A. M. Van Harten, Mutation Breeding, Theory and Practical Applications. 1988. Cambridge University Press.*

Gosling, ed, "The *Chrysanthemum* Manual" 1979. 6$^{th}$ edition, The National *Chrysanthemum* Society, London, Essex Telegraph Press, Ltd, pp. 329–336.*

Dowrick et al. "The induction of mutations in *Chrysanthemum* using x– and gamma radiation", 1966, Euphytica, 15:204–210.*

* cited by examiner

*Primary Examiner*—Kent Bell
*Assistant Examiner*—Annette H Para
(74) *Attorney, Agent, or Firm*—Knobbe Martens Olson & Bear LLP

(57) ABSTRACT

A new and distinct *Chrysanthemum* plant cultivar is disclosed, characterized by having a pink and yellow-colored spider-type flower with a longevity of about 26 days. The plant has a mounding, free-branching growth habit, and naturally blooms beginning the first week of September.

1 Drawing Sheet

Figure 1:
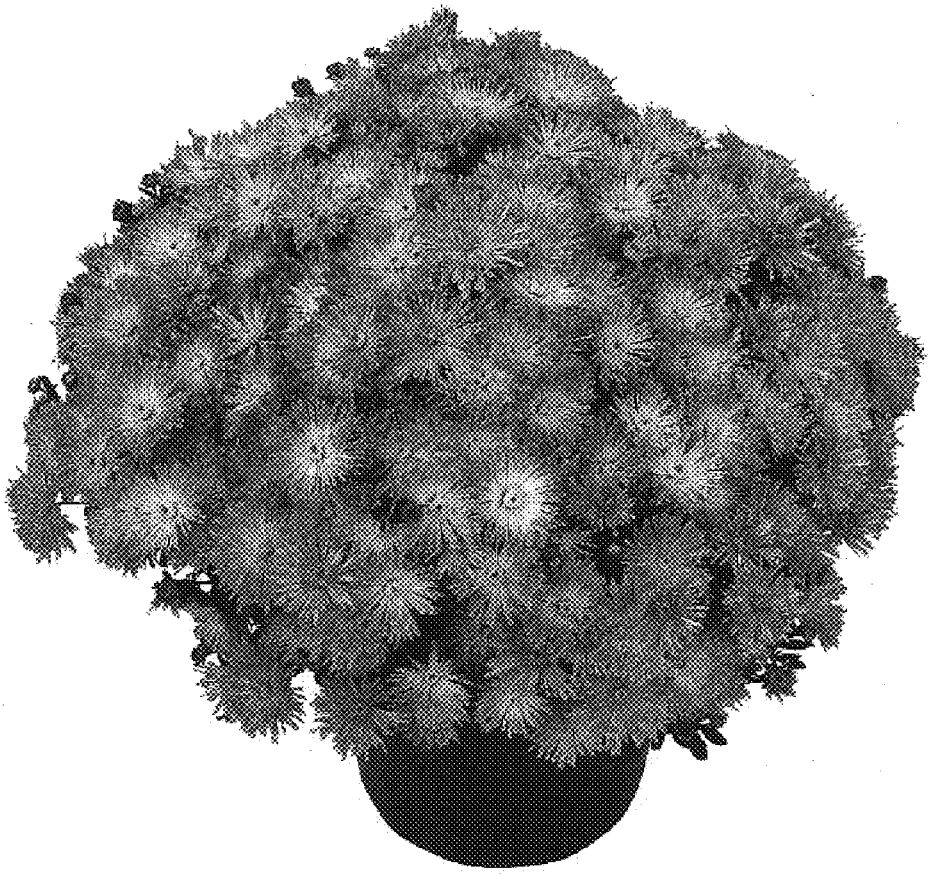

Latin name of the genus and species: *Chrysanthemum morifolium.*
Variety denomination: 'GEDI THREE CAMAN'.

BACKGROUND OF THE INVENTION

The new cultivar 'GEDI THREE CAMAN' is a product of an induced mutation of the parent *Chrysanthemum* plant variety 'GEDI TWO AMA' (U.S. Plant Pat. No. 14,950) using gamma ray treatment at a dose of 20 Gy. The new cultivar 'GEDI THREE CAMAN' was discovered and selected by Dirk Pieters in a controlled environment in Oostnieuwkerke, Belgium during October, 2001.

Asexual reproduction of the new cultivar 'GEDI THREE CAMAN' by terminal cuttings and tissue culture was performed in Oxnard, Calif. and has shown that the unique features of this cultivar are stable and reproduced true to type on successive generations.

SUMMARY OF THE INVENTION

The cultivar 'GEDI THREE CAMAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GEDI THREE CAMAN.' These characteristics in combination distinguish 'GEDI THREE CAMAN' as a new and distinct *Chrysanthemum* cultivar:

1. Pink/Yellow spider-type flower.
2. Floral longevity of about 26 days.

3. Mounding growth habit.
4. Free-branching.
5. Average plant vigor.
6. Naturally blooms beginning the first week of September.

Plants of the new cultivar 'GEDI THREE CAMAN' are similar to plants of the parent variety, 'GEDI TWO AMA' in most horticultural characteristics, however plants of the new cultivar 'GEDI THREE CAMAN' have ray florets that are a different color than the ray florets of the parent variety 'GEDI TWO AMA'.

In comparison to the commercially available variety 'GEDI ONE TAR' (U.S. Plant Pat. No. 13,689), the new variety 'GEDI THREE CAMAN' has a larger diameter flower and ray florets that are of a different color. Additionally, the new variety 'GEDI THREE CAMAN' has more ray florets than the comparable variety 'GEDI ONE TAR.' Further, the new variety 'GEDI THREE CAMAN' is taller than the comparable variety 'GEDI ONE TAR.'

In comparison to the commercially available variety 'YOMAGGIE' (U.S. Plant Pat. No. 11,855), 'GEDI THREE CAMAN' has more numerous, different colored ray florets. Additionally, the new variety 'GEDI THREE CAMAN' has more flowers per flowering stem than the comparable variety 'YOMAGGIE.' Further, the new variety is taller and naturally blooms three to four weeks earlier than the comparable variety 'YOMAGGIE.'

BRIEF DESCRIPTION OF THE PHOTOGRAPH

The accompanying photograph in FIG. 1 illustrates in full color a typical plant of 'GEDI THREE CAMAN' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GEDI THREE CAMAN' plants grown in a greenhouse in Oxnard, Calif., during the month of September, 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere.

Botanical classification: *Chrysanthemum morifolium* 'GEDI THREE CAMAN.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 36 cm.
Plant spread: Approximately 42 cm.
Growth rate: Moderate.
Branching characteristics: Free branching.
Length of lateral branches: Approximately 32 cm.
Number of leaves per lateral branch: Approximately 27.
Age of plant described: Approximately 105 days from a rooted cutting.

FOLIAGE

Leaf:
- *Arrangement.*—Alternate.
- *Average length.*—Approximately 4.1 cm.
- *Average width.*—Approximately 3.1 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 3.2 cm.
- *Color.*—Young foliage upper side: Near Green 137A. Young foliage under side: Near Green 137A. Mature foliage upper side: Near Yellow-green 147A. Mature foliage under side: Near Yellow-green 147A.
- *Venation.*—Type: Palmately net. Venation color upper side: Near Yellow-green 146C. Venation color under side: Near Yellow-green 146C.

Petiole:
- *Average length.*—Approximately 1.0 cm.
- *Color.*—Near Yellow-green 146C.
- *Diameter.*—Approximately 0.2 cm.

BLOOM

Flower:
- *Flowering habit.*—Induced by darkness period greater than approximately 13.5 hours, approximately 42 days of approximate day length required to induce and develop blooms.
- *Form.*—Spider.
- *Natural flowering season.*—Approximately the first week of September.
- *Number of flowers per lateral branch.*—Approximately 32.
- *Diameter.*—Approximately 5.4 cm.
- *Depth.*—Approximately 1.7 cm.
- *Longevity on plant.*—Approximately 26 days.
- *Persistence.*—Persistent.

Ray florets:
- *Appearance.*—Matte.
- *Texture.*—Smooth.
- *Average number of ray florets per flower.*—Approximately 320.
- *Shape.*—Oblong.
- *Aspect.*—Cylindric.
- *Margin.*—Entire.
- *Apex.*—Rounded.
- *Length.*—Approximately 2.7 cm.
- *Width.*—Approximately 0.3 cm.
- *Color.*—Upper surface at first opening: Near Red 37A. Upper surface at maturity: Near Red 41C upper 80%, near Yellow 8B lower 20%. Upper surface at fading: Near Red 41C upper 60%, Near Yellow 8D lower 40%. Under surface at first opening: Near Orange-red 35B. Under surface at maturity: Near Red 41C. Under surface at fading: Near Red 41D.

Disc florets:
- *Appearance.*—Shiny.
- *Texture.*—Smooth.
- *Average number of florets per disc.*—Approximately 25.
- *Shape.*—Cylindric.
- *Apex.*—Obtuse.
- *Average length.*—Approximately 0.5 cm.
- *Average width.*—Approximately 0.1 cm.
- *Color.*—At first opening: Near Yellow 7C. At maturity: Near Yellow 8B. At fading: Near Yellow-orange 15D.

Peduncle:
- *Length.*—At terminal end (shortest): Approximately 4.2 cm. At lateral end (longest): Approximately 7.2 cm.
- *Angle to stem.*—Acute.
- *Strength.*—Moderate.
- *Color.*—Near Yellow-green 147B.
- *Habit.*—Upright.
- *Diameter.*—Approximately 0.2 cm.
- *Surface texture.*—Lightly pubescent.

Flower bud:
- *Length.*—Approximately 0.8 cm.
- *Diameter.*—Approximately 0.8 cm.
- *Form.*—Globular.
- *Color.*—Near Orange-red 35B.

Involucral bracts (phyllaries):
- *Appearance.*—Matte.
- *Texture.*—Lightly pubescent.
- *Number.*—Approximately 35.
- *Shape.*—Oblanceolate.
- *Margin.*—Entire.
- *Apex.*—Acute.
- *Length.*—Approximately 0.8 cm.
- *Width.*—Approximately 0.4 cm.
- *Color.*—Upper side: Near Green 137A. Under side: Near Green 137A.

REPRODUCTIVE ORGANS

Ray florets:

*Number of pistils per floret.*—1.
*Stigma shape.*—2 branched.
*Stigma color.*—Near Yellow 4C.
*Style color.*—Near Yellow 4D.
*Style length.*—Approximately 0.4 cm.
*Stamens.*—Absent.

Disc florets:

*Number of pistils per floret.*—1.
*Stigma shape.*—Two-branched.
*Stigma color.*—Near Yellow 2A.
*Style length.*—Approximately 0.3 cm.
*Style color.*—Near Yellow-green 154D.
*Number of stamens per floret.*—Approximately 5.
*Anther shape.*—Tubular.
*Anther color.*—Near Yellow 11A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperature about −2° C. Non-flowering plants are hardy in the approximately range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'GEDI THREE CAMAN' as herein illustrated and described.

* * * * *